US008802103B2

(12) United States Patent
Gurney et al.

(10) Patent No.: US 8,802,103 B2
(45) Date of Patent: Aug. 12, 2014

(54) COMPOSITIONS AND METHODS FOR DIAGNOSING AND TREATING CANCER

(75) Inventors: Austin Gurney, San Francisco, CA (US); Timothy Hoey, Hillsborough, CA (US); Sanjeev Satyal, San Carlos, CA (US); Maureen Fitch Bruhns, San Mateo, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 328 days.

(21) Appl. No.: 12/121,348

(22) Filed: May 15, 2008

(65) Prior Publication Data

US 2008/0317760 A1     Dec. 25, 2008

Related U.S. Application Data

(60) Provisional application No. 60/938,059, filed on May 15, 2007.

(51) Int. Cl.
*A61K 39/395* (2006.01)
*C07K 16/18* (2006.01)
*C07K 16/22* (2006.01)
*C07K 16/32* (2006.01)

(52) U.S. Cl.
USPC .................. 424/181.1; 424/130.1; 424/133.1; 424/134.1; 424/138.1; 424/141.1; 424/142.1; 424/145.1; 424/152.1; 424/155.1; 424/156.1; 424/172.1; 424/174.1; 424/179.1; 530/387.3; 530/387.7; 530/388.1; 530/388.15; 530/388.23; 530/388.24; 530/388.8; 530/388.85; 530/391.1; 530/391.3; 530/391.7

(58) Field of Classification Search
USPC .......... 424/130.1, 133.1, 134.1, 138.1, 141.1, 424/142.1, 145.1, 152.1, 155.1, 156.1, 424/172.1, 174.1, 179.1, 181.1; 530/387.3, 530/387.7, 388.1, 388.15, 388.23, 388.24, 530/388.8, 388.85, 391.1, 391.3, 391.7
See application file for complete search history.

(56) References Cited

U.S. PATENT DOCUMENTS

| 5,789,195 | A |   | 8/1998  | Artavanis-Tsakonas et al. |
|-----------|---|---|---------|---------------------------|
| 5,856,441 | A |   | 1/1999  | Artavanis-Tsakonas et al. |
| 5,869,282 | A |   | 2/1999  | Ish-Horowicz et al. |
| 6,004,924 | A |   | 12/1999 | Ish-Horowicz et al. |
| 6,083,904 | A |   | 7/2000  | Artavanis-Tsakonas |
| 6,136,952 | A | * | 10/2000 | Li et al. ..................... 530/326 |
| 6,337,387 | B1 |  | 1/2002  | Sakano et al. |
| 6,433,138 | B1 |  | 8/2002  | Zimrin et al. |
| 6,689,744 | B2 |  | 2/2004  | Gao et al. |
| 6,703,489 | B1 |  | 3/2004  | Ish-Horowicz |
| 6,716,974 | B1 |  | 4/2004  | Maciag et al. |
| 6,825,007 | B2 |  | 11/2004 | Zimrin et al. |
| 7,115,360 | B2 |  | 10/2006 | Clarke et al. |

| 2003/0185829 | A1 | 10/2003 | Koller et al. |
|---|---|---|---|
| 2003/0194804 | A1 | 10/2003 | Lamb et al. |
| 2004/0253602 | A1 | 12/2004 | Maciag et al. |
| 2005/0003406 | A1 | 1/2005 | Coignet |
| 2005/0025751 | A1 | 2/2005 | Bodmer et al. |
| 2005/0026831 | A1 | 2/2005 | Bodmer et al. |
| 2005/0129686 | A1 | 6/2005 | Coignet |
| 2005/0137130 | A1 | 6/2005 | Bodmer et al. |
| 2005/0220886 | A1 | 10/2005 | Bodmer et al. |
| 2005/0239064 | A1 | 10/2005 | Artavanis-Tsakonas et al. |
| 2005/0261477 | A1 | 11/2005 | Champion et al. |
| 2006/0034857 | A1 | 2/2006 | Lamb et al. |
| 2006/0084588 | A1 | 4/2006 | Briend et al. |
| 2007/0036800 | A1 | 2/2007 | Bergstein |
| 2007/0036801 | A1 | 2/2007 | Bergstein |
| 2007/0036802 | A1 | 2/2007 | Bergstein |
| 2007/0036803 | A1 | 2/2007 | Bergstein |
| 2007/0036804 | A1 | 2/2007 | Bergstein |
| 2007/0041984 | A1 | 2/2007 | Bergstein |

FOREIGN PATENT DOCUMENTS

| EP | 0861894 B1 | 3/2006 |
|---|---|---|
| EP | 1175909 B1 | 3/2009 |
| WO | WO 2004/091383 A2 | 10/2004 |
| WO | WO 2009/124931 A2 | 10/2009 |

OTHER PUBLICATIONS

Jain (Scientific American Jul. 1994 p. 58-65).*
Dillman (Annals of Internal Medicine, vol. 111, pp. 592-603, 1989.*
Weiner (Seminars Oncology, vol. 26, No. 4, 1999, pp. 41-50.*
Santagata et al (Cancer Res. 2004; 64:6854-6857).*
Choi, J.-H., et al., "Jagged-1 and Notch3 Juxtacrine Loop Regulates Ovarian Tumor Growth and Adhesion", *Cancer Res* 68:5716-5723, American Association for Cancer Research (2008).
Gray, G.E., et al., "Human Ligands of the Notch Receptor", *American Journal of Pathology* 154:785-794, American Society for Investigative Pathology (1999).
Gridley, T., "Review: Notch Signaling in Vertebrate Development and Disease", *Molecular and Cellular Neuroscience* 9:103-108, Academic Press (1997).
Iso, T., et al., "Notch Signaling in Vascular Development", *Arterioscler Throm Vasc Biol.* 23:543-553, American Heart Association, Inc. (2003).
Joutel, A. and Tournier-Lasserve, E., "Notch signalling pathway and human diseases", *Cell & Development Biology* 9:619-625, Academic Press (1998).
Karanu, F.N., et al., "The Notch Ligand Jagged-1 Represents a Novel Growth Factor of Human Hematopoietic Stem Cells", *J. Exp. Med.* 192:1365-1372, The Rockefeller University Press (2000).

(Continued)

*Primary Examiner* — Ram R Shukla
*Assistant Examiner* — Anne Holleran
(74) *Attorney, Agent, or Firm* — Sterne, Kessler, Goldstein & Fox P.L.L.C.

(57) ABSTRACT

Monoclonal antibodies that specifically bind to an extracellular domain of human Jagged 1 and inhibit growth of a tumor comprising cancer stem cells are described. Also described is a method of treating cancer that comprises administering a therapeutically effective amount of a monoclonal anti-Jagged 1 antibody.

14 Claims, 4 Drawing Sheets

(56) References Cited

OTHER PUBLICATIONS

Figure 1:
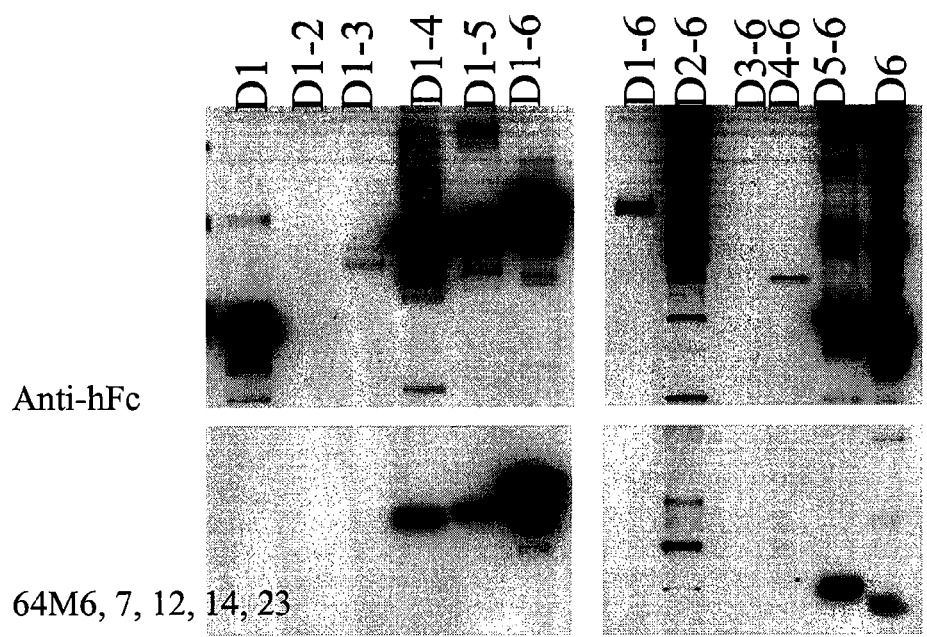

Kopper, L. and Hajdú, M., "Tumor Stem Cells", *Pathology Oncology Research* 10:69-73, Arányi Lajos Foundation (2004).

Li, L., et al., "Alagille syndrome is caused by mutations in human *Jagged1*, which encodes a ligand for Notch1", *Nature Genetics* 16:243-251, Nature America Inc. (1997).

"Mouse Monoclonal anti-Jag1 (1E12)", Novus Biologicals, Inc., available at http://www.novusbio.com/data_sheet/pdf_data_sheet/53889, 2 pages, released 2006.

Purow, B.W., et al., "Expression of Notch-1 and Its Ligands, Delta-Like-1 and Jagged-1, Is Critical for Glioma Cell Survival and Proliferation", *Cancer Res* 65:2353-2363, American Association for Cancer Research (Mar. 2005).

Rugo, H.S., "Bevacizumab in the Treatment of Breast Cancer: Rationale and Current Data", *The Oncologist* 9:43-49, AlphaMed Press (2004).

Santagata, S., et al., "JAGGED1 Expression Is Associated with Prostate Cancer Metastasis and Recurrence", *Cancer Res* 64:6854-6857, American Association for Cancer Research (2004).

Shi, W. and Harris, A.L., "Notch Signaling in Breast Cancer and Tumor Angiogenesis: Cross-Talk and Therapeutic Potentials", *J. Mammary Gland Biol Neoplasia* 11:41-52, Springer (Jan. 2006).

Zhang, Y., et al., "Down-regulation of Jagged-1 induces cell growth inhibition and S phase arrest in prostate cancer cells", *Int. J. Cancer* 119:2071-2077, Wiley-Liss, Inc. (Nov. 2006).

International Search Report and Written Opinion of the International Searching Authority for International Application No. PCT/US08/06173, mailed Jul. 17, 2008, ISA/US, Alexandria, Virginia, U.S.A.

Nehring, L., et al., "The extracellular matrix protein MAGP-2 interacts with Jagged1 and induces its shedding from the cell surface," *J. Biol. Chem.* 280:20349-20355, American Society for Biochemistry and Molecular Biology, US (2005).

Sall, W., Md, "Bevacizubmab (Avastin) in Advanced Prostate Cancer," Chemotherapy Foundation Symposium 2003, Nov. 14, 2003, New York, New York, US.

Li, L., et al., "The Human Homolog of Rat *Jagged*1 Expressed by Marrow Stroma Inhibits Differentiation of 32D Cells through Interaction with Notch1," *Immunity* 8: 43-55, Cell Press, United States (Jan. 1998).

Lindsell, C.E., et al., "Jagged: A Mammalian Ligand That Activates Notch1," *Cell* 80: 909-917, Cell Press, United States (Mar. 1995).

* cited by examiner

Figure 2
64M14 Anti-Jagged 1 Blocks Binding of Human and Rat Jagged 1 to Notch 1
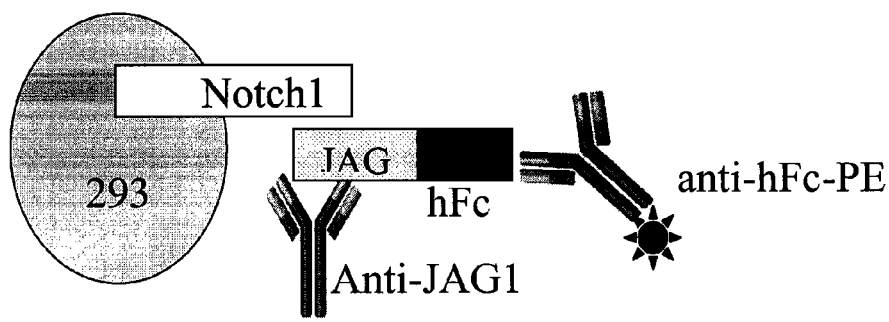
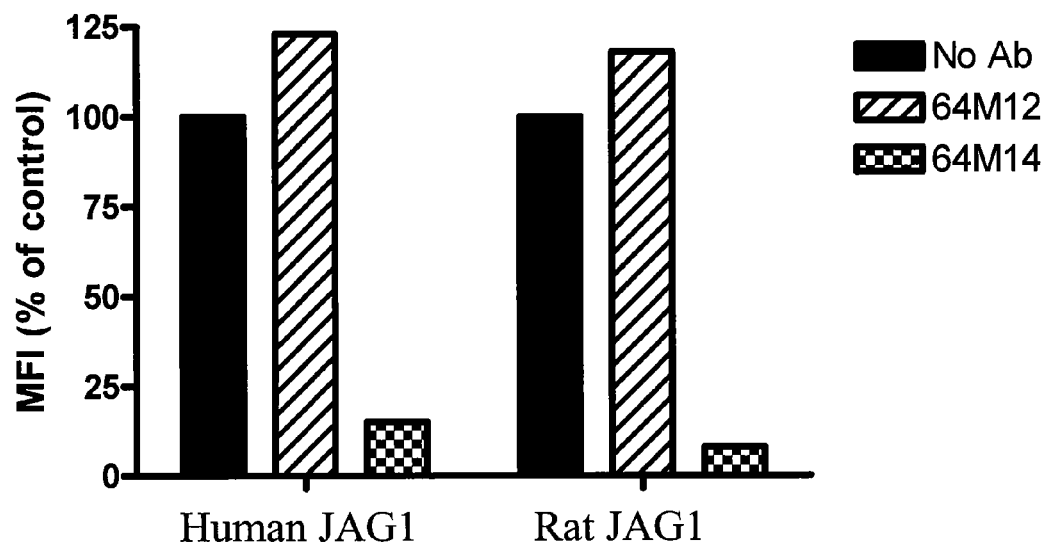

COMPOSITIONS AND METHODS FOR DIAGNOSING AND TREATING CANCER

CROSS-REFERENCE TO RELATED APPLICATIONS

This application claims the benefit of U.S. Prov. Appl. No. 60/938,059, filed May 15, 2007 which is herein incorporated by reference.

BACKGROUND OF THE INVENTION

1. Field of the Invention

The present invention relates to the field of oncology and provides novel compositions and methods for diagnosing and treating cancer. The present invention provides antibodies against a cancer stem cell marker for the diagnosis and treatment of solid tumors.

2. Background Art

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, Cancer J. Clin. 53:5-26).

Breast cancer is the most common cancer in women, with an estimated 12% of women at risk of developing the disease during their lifetime. Although mortality rates have decreased due to earlier detection and improved treatments, breast cancer remains a leading cause of death in middle-aged women, and metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases (American Joint Committee on Cancer: AJCC Cancer Staging Manual. Philadelphia, Pa.: Lippincott-Raven Publishers, 5th ed., 1997, pp 171-180; Harris, J R: "Staging of breast carcinoma" in Harris, J. R., Hellman, S., Henderson, I. C., Kinne D. W. (eds.): Breast Diseases. Philadelphia, Lippincott, 1991). These parameters are used to provide a prognosis and select an appropriate therapy. The morphologic appearance of the tumor can also be assessed but because tumors with similar histopathologic appearance can exhibit significant clinical variability, this approach has serious limitations. Finally assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., 2003, CA Cancer J. Clin. 53:5-26). Since the introduction of the prostate specific antigen (PSA) blood test, early detection of prostate cancer has dramatically improved survival rates; the five year survival rate for patients with local and regional stage prostate cancers at the time of diagnosis is nearing 100%. Yet more than 50% of patients will eventually develop locally advanced or metastatic disease (Muthuramalingam et al., 2004, Clin. Oncol. 16:505-16).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., 2004, Clin. Oncol. 16:505-16; Trojan et al., 2005, Anticancer Res. 25:551-61).

Colorectal cancer is the third most common cancer and the fourth most frequent cause of cancer deaths worldwide (Weitz et al., 2005, Lancet 365:153-65). Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinomas invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through the muscularis propria and may penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50% and is now the standard of care for these patients.

Lung cancer is the most common cancer worldwide, the third most commonly diagnosed cancer in the United States, and by far the most frequent cause of cancer deaths (Spiro et al., 2002, Am. J. Respir. Crit. Care Med. 166:1166-96; Jemal et al., 2003, CA Cancer J. Clin. 53:5-26). Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%.

Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., 2002, *Am. J. Respir. Crit. Care Med.* 166:1166-96).

These four cancers, as well as many others, present as solid tumors that are composed of heterogeneous cell populations. For example, breast cancers are a mixture of cancer cells and normal cells, including mesenchymal (stromal) cells, inflammatory cells, and endothelial cells. Several models of cancer provide different explanations for the presence of this heterogeneity. One model, the classic model of cancer, holds that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells have some degree of tumorigenic potential. (Pandis et al., 1998, *Genes, Chromosomes & Cancer* 12:122-129; Kuukasjrvi et al., 1997, *Cancer Res.* 57:1597-1604; Bonsing et al., 1993, *Cancer* 71:382-391; Bonsing et al., 2000, *Genes Chromosomes & Cancer* 82: 173-183; Beerman H et al., 1991, *Cytometry* 12:147-54; Aubele M & Werner M, 1999, *Analyt. Cell. Path.* 19:53; Shen L et al., 2000, *Cancer Res.* 60:3884).

An alternative model for the observed solid tumor cell heterogeneity derives from the impact of stem cells on tumor development. According to this model, cancer arises from dysregulation of the mechanisms that control normal tissue development and maintenance. (Beachy et al., 2004, *Nature* 432:324). During normal animal development, cells of most or all tissues are derived from normal precursors, called stem cells (Morrison et al., 1997, *Cell* 88:287-98; Morrison et al., 1997, *Curr. Opin. Immunol.* 9:216-21; Morrison et al., 1995, *Annu. Rev. Cell. Dev. Biol.* 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-studied example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain. Tumors derived from a "solid tumor stem cell" (or "cancer stem cell" from a solid tumor) subsequently undergo chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, *Nature* 17:645-8). More recently it has been demonstrated that malignant human breast tumors similarly harbor a small, distinct population of cancer stem cells enriched for the ability to form tumors in immunodeficient mice. An ESA+, CD44+, CD24-/low, Lin-cell population was found to be 50-fold enriched for tumorigenic cells compared to unfractionated tumor cells (Al-Hajj et al., 2003, *Proc. Nat'l Acad. Sci.* 100:3983-8). The ability to prospectively isolate the tumorigenic cancer cells has permitted investigation of critical biological pathways that underlie tumorigenicity in these cells, and thus promises the development of better diagnostic assays and therapeutics for cancer patients

BRIEF SUMMARY OF THE INVENTION

Provided are antibodies against the Notch receptor ligand Jagged 1. Also provided are pharmaceutical compositions comprising the antibodies of the present disclosure and a pharmaceutically acceptable vehicle. Further provided are methods of treating cancer comprising administering anti-Jagged 1 antibodies of the present disclosure in an amount effective to inhibit tumor cell growth.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory only and are not restrictive of the invention, as claimed. The accompanying drawings, which are incorporated in and constitute a part of this specification, illustrate several embodiments of the invention and, together with the description, serve to explain the principles of the invention. In the specification and the appended claims, the singular forms "a," "an," and "the" include plural reference unless the context clearly dictates otherwise.

BRIEF DESCRIPTION OF THE DRAWINGS/FIGURES

FIG. 1: Epitope mapping of anti-Jagged 1 monoclonal antibodies. Fc fusion proteins containing a deletion series of Jagged 1 EGF domains were separated by SDS-PAGE and blotted with monoclonal antibodies 64M6, 64M7, 64M12, 64M14 and 64M23. Deletion constructs from left to right are as follows: Left gel C-terminal deletions D1 (amino acids 31-113); D1-2 (a.a. 31-165); D1-3 (a.a. 31-230); D1-4 (a.a. 31-263); D1-5 (a.a. 31-296); and D1-6 (a.a. 31-335) and right gel N-terminal deletions D2-6 (a.a. 114-335); D3-6 (a.a. 166-335); D4-6 (a.a. 230-335); D5-6 (a.a. 265-335); and D6 (a.a. 297-335). In contrast to anti-hFc antibodies that detected fusion proteins in all lanes, antibodies 64M6, 64M7, 64M12, 64M14 and 64M23 only detected fusion proteins containing Domain 4 (EGF1).

FIG. 2: Anti-Jagged 1 antibodies block Notch ligand binding. Anti-Jagged 1 64M14 antibodies (diagonal lines) inhibited binding of either human (left) or rat (right) Jagged 1 extracellular domain Fc-fusion proteins to Notch 1 expressed in 293 cells. Binding was detected using an anti-hFc antibody linked to PE by FACS, and MFI is graphed based on the percentage of binding detected compared to no antibody control (black). In contrast, 64M12 anti-Jagged 1 antibodies had no effect on Jagged 1 binding to Notch 1 (checkered).

Figure 3:
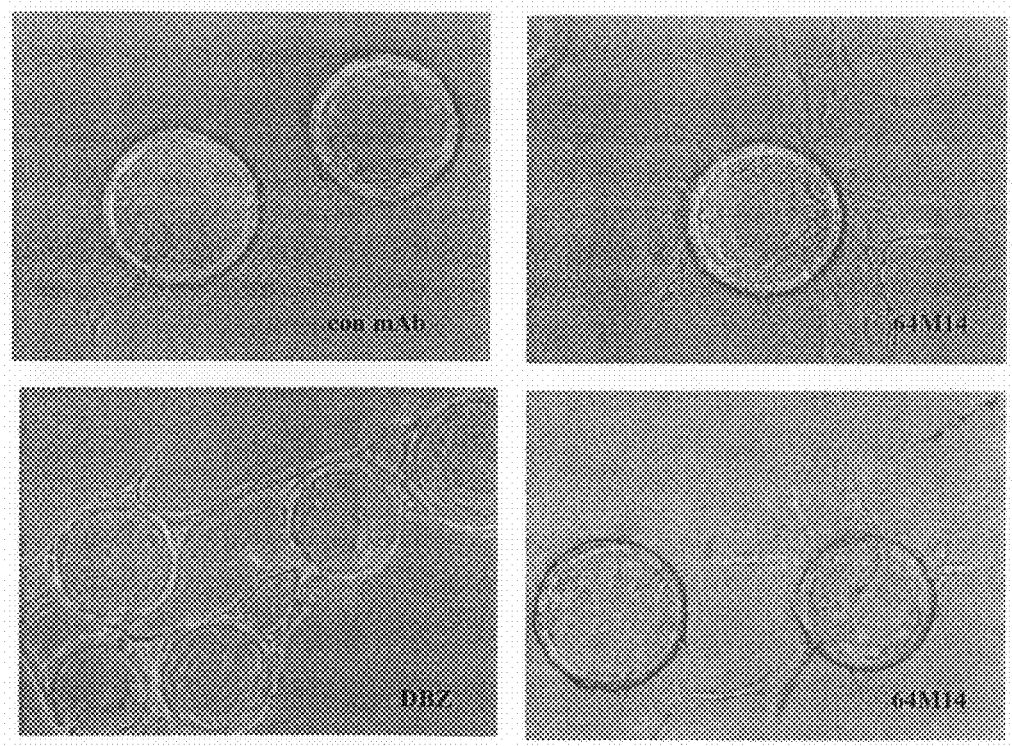

FIG. 3: Anti-Jagged 1 antibodies enhance endothelial cell sprouting. HBMVECs co-cultured with skin fibroblasts in fibrin gels showed little sprouting in the presence of a control antibody (con mAb, upper left panel). In contrast, incubation with 64M14 anti-Jagged 1 antibodies (upper and lower right panels) resulted in a similar increase in sprouting as observed with a gamma-secretase inhibitor DBZ (lower left panel).

Figure 4:
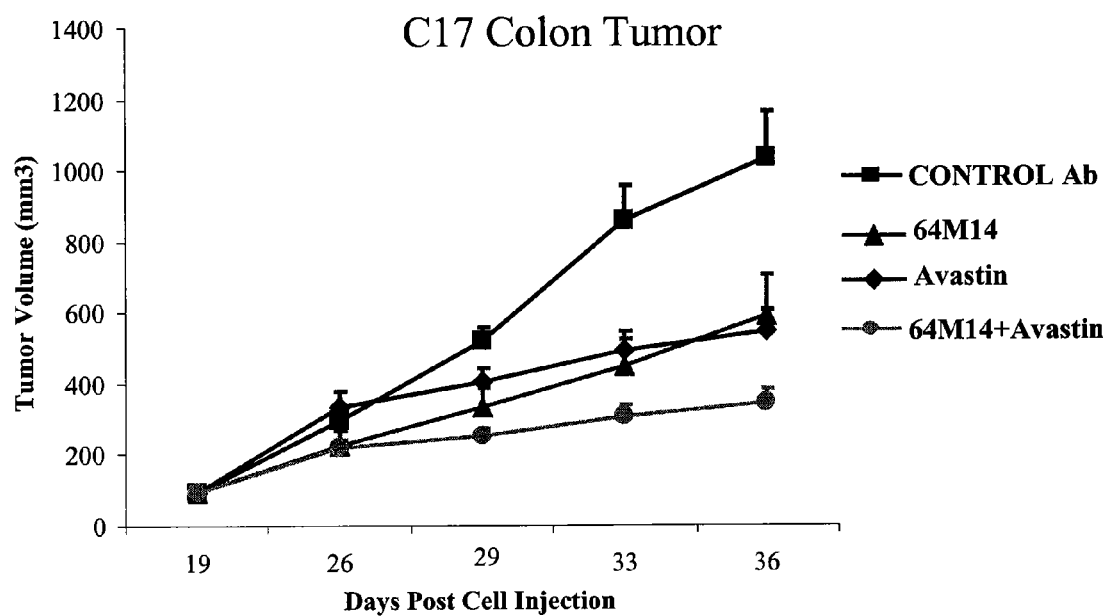

FIG. 4: Anti-Jagged 1 antibodies reduce the growth of colon tumor cells. UM-C17 tumors in NOD/SCID mice showed close to 50% reduction in growth when treated with either 10 mg/kg 64M14 anti-Jagged 1 antibodies (triangles) or 10 mg/kg Avastin (diamonds) as compared to control antibodies (squares). Combined treatment with 10 mg/kg 64M14 anti-Jagged 1 antibodies plus 10 mg/kg Avastin reduced tumor growth better than either antibody alone (circles).

DETAILED DESCRIPTION OF THE INVENTION

The term "antibody" is used to mean an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In certain embodiments, antibodies of the present invention include antagonist antibodies that specifically bind to a cancer stem cell marker protein and interfere with, for example, ligand binding, receptor dimerization, expression of a cancer stem cell marker protein, and/or downstream signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, antibody internalization and/or recognized by the immune system. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "humanized antibody" refers to forms of non-human (e.g. rodent) antibodies that are specific immunoglobulin chains, chimeric immunoglobulins, or fragments thereof that contain minimal non-human sequences. Typically, humanized antibodies are human immunoglobulins in which residues from the complementary determining regions (CDRs) within the antigen determination region (or hypervariable region) of the variable region of an antibody chain or chains are replaced by residues from the CDR of a non-human species (e.g. mouse, rat, rabbit, hamster) that have the desired specificity, affinity, and capability. In some instances, residues from the variable chain framework region (FR) of a human immunoglobulin are replaced with the corresponding residues in an antibody from a non-human species that has the desired specificity, affinity, and capability. The humanized antibody can be further modified by the substitution of additional residue either in the variable framework region and/or within the replaced non-human residues to refine and optimize antibody specificity, affinity, and/or capability. In general, the humanized antibody will comprise substantially all of at least one, and typically two or three or four, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Molec. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means, for instance, that an antibody binds to a protein with a $K_D$ of at least about 0.1 mM, but more usually at least about 1 μM. "Selectively binds" or "specifically binds" means at times that an antibody binds to a protein at times with a $K_D$ of at least about 0.1 μM or better, and at other times at least about 0.01 μM or better. Because of the sequence identity between homologous proteins in different species, specific binding can include an antibody that recognizes a cancer stem cell marker protein in more than one species.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

The terms "isolated" or "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g. an antibody) or nucleic acid of the present disclosure that is the predominant species present in a preparation is substantially purified. In particular, an isolated nucleic acid is separated from open reading frames that naturally flank the gene and encode proteins other than protein encoded by the gene. An isolated antibody is separated from other non-immunoglobulin proteins and from other immunoglobulin proteins with different antigen binding specificity. It can also mean that the nucleic acid or protein is in some embodiments at least 80% pure, in some embodiments at least 85% pure, in some embodiments at least 90% pure, in some embodiments at least 95% pure, and in some embodiments at least 99% pure.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell", "tumor stem cell", or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. Solid tumor stem cells differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004, 528 proposes that such a model can be used to enhance the diagnosis of cancer. The solid tumor stem cell model is fundamentally different from the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while solid tumor stem cells are cancer cells that may themselves contain the mutations that are responsible for tumorigenesis starting at the pre-cancerous stage through later stage cancer. That is, solid tumor stem cells ("cancer stem cells") would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment) where they still form new tumors distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

The terms "cancer cell", "tumor cell" and grammatical equivalents refer to the total population of cells derived from a tumor or a pre-cancerous lesion including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "biopsy" or "biopsy tissue" refer to a sample of tissue or fluid that is removed from a subject for the purpose of determining if the sample contains cancerous tissue. In some embodiments, biopsy tissue or fluid is obtained because a subject is suspected of having cancer, and the biopsy tissue or fluid is then examined for the presence or absence of cancer.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

"Prodrug" refers to a derivative of a therapeutically effective compound that requires a transformation within the body to produce the therapeutically effective compound. Prodrugs can be pharmacologically inactive until converted to the therapeutically effective parent compound.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

As used herein, "providing a diagnosis" or "diagnostic information" refers to any information, including for example the presence of cancer stem cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information, including for example the presence of cancer stem cells in a subject's tumor, regarding the impact of the presence of cancer (e.g., as determined by the diagnostic methods of the present invention) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; or some combination of effects.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA, including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl 2-thiouracil, 5-carboxymethylaminomethyluracil, dihydrouracil, inosine, N6 isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl 2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2 thiouracil, 2-thiouracil, 4-thiouracil, 5-methyluracil, N-uracil 5-oxyacetic acid methylester, uracil-5-oxyacetic acid, pseudouracil, queosine, 2-thiocytosine, and 2,6-diaminopurine.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

"Ligation" refers to the process of forming phosphodiester bonds between two double stranded nucleic acid fragments. Unless otherwise provided, ligation can be accomplished using known buffers and conditions with 10 units to T4 DNA ligase ("ligase") per 0.5 ug of approximately equimolar amounts of the DNA fragments to be ligated. Ligation of nucleic acid can serve to link two proteins together in-frame to produce a single protein, or fusion protein.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "epitope tagged" as used herein refers to a chimeric polypeptide comprising a cancer stem cell marker protein, or a domain sequence or portion thereof, fused to an "epitope tag". The epitope tag polypeptide comprises enough amino acid residues to provide an epitope for recognition by an antibody, yet is short enough such that it does not interfere with the activity of the cancer stem cell marker protein. Suitable epitope tags generally have at least six amino acid residues, usually between about 8 to about 50 amino acid residues, and at times between about 10 to about 20 residues. Commonly used epitope tags include Fc, HA, His, and FLAG tags.

The present invention provides compositions and methods for studying, diagnosing, characterizing, and treating cancer. In particular, the present invention provides antibodies against solid tumor stem cell markers and methods of using these antibodies to inhibit tumor growth and treat cancer in human patients. In certain embodiments, antibodies of the present invention include antagonist antibodies that specifically bind to a cancer stem cell marker protein and interfere with, for example, ligand binding, receptor dimerization, expression of a cancer stem cell marker protein, and/or signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, internalization and/or recognized by the immune system. In certain embodiments, the antibodies specifically recognize more than one solid tumor stem cell marker protein.

Like the tissues in which they originate, solid tumors consist of a heterogeneous population of cells. That the majority of these cells lack tumorigenicity suggested that the development and maintenance of solid tumors also relies on a small population of stem cells (i.e., tumorigenic cancer cells) with the capacity to proliferate and efficiently give rise both to additional tumor stem cells (self-renewal) and to the majority of more differentiated tumor cells that lack tumorigenic potential (i.e., non-tumorigenic cancer cells). The concept of cancer stem cells was first introduced soon after the discovery of hematopoietic stem cells (HSC) and was established experimentally in acute myelogenous leukemia (AML) (Park et al., 1971, *J. Natl. Cancer Inst.* 46:411-22; Lapidot et al., 1994, *Nature* 367:645-8; Bonnet & Dick, 1997, *Nat. Med.* 3:730-7; Hope et al., 2004, *Nat. Immunol.* 5:738-43). Stem cells from solid tumors have more recently been isolated based on their expression of a unique pattern of cell-surface receptors and on the assessment of their properties of self-renewal and proliferation in culture and in xenograft animal models. An ESA+CD44+CD24-/low Lineage-population greater than 50-fold enriched for the ability to form tumors relative to unfractionated tumor cells was discovered (Al-Hajj et al., 2003, *Proc. Nat'l. Acad. Sci.* 100:3983-8). The ability to isolate tumorigenic cancer stem cells from the bulk of non-tumorigenic tumor cells has led to the identification of cancer stem cell markers, genes with differential expression in cancer stem cells compared to non-tumorigenic tumor cells or normal breast epithelium, using microarray analysis. One embodiment of the present invention employs the knowledge of these identified cancer stem cell markers to diagnosis and treat cancer.

The cancer stem cell markers of the present invention relate to human Jagged 1, a Notch receptor ligand. The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it can alter the developmental fate of tumor cells to maintain them in an undifferentiated and proliferative state (Brennan and Brown, 2003, *Breast Cancer Res.* 5:69). Thus carcinogenesis can proceed by usurping homeostatic mechanisms controlling normal development and tissue repair by stem cell populations (Beachy et al., 2004, *Nature* 432:324).

The Notch receptor was first identified in *Drosophila* mutants. Haploinsufficiency of *Drosophila* Notch results in notches at the wing margin whereas loss-of-function produces an embryonic lethal "neurogenic" phenotype where cells of the epidermis switch fate to neural tissue (Moohr, 1919, *Genet.* 4:252; Poulson, 1937, *PNAS* 23:133; Poulson, 1940, *J. Exp. Zool.* 83:271). The Notch receptor is a single-pass transmembrane receptor containing numerous tandem epidermal growth factor (EGF)-like repeats and cysteine-rich Notch/LIN-12 repeats within a large extracellular domain (Wharton et al., 1985, *Cell* 43:567; Kidd et al., 1986, *Mol. Cell. Biol.* 6:3094; reviewed in Artavanis et al., 1999, *Science* 284:770). Four mammalian Notch proteins have been identified (NOTCH1, NOTCH2, NOTCH3, and NOTCH4), and mutations in these receptors invariably result in developmental abnormalities and human pathologies including several cancers as described in detail below (Gridley, 1997, *Mol. Cell. Neurosci.* 9:103; Joutel & Tournier-Lasserve, 1998, *Semin. Cell Dev. Biol.* 9:619-25).

The Notch receptor is activated by single-pass transmembrane ligands of the Delta, Serrated, Lag-2 (DSL) family. The known Notch ligands in mammals, Delta-like 1 (D111), Delta-like 3 (D113), Delta-like 4 (D114), Jagged 1 and Jagged 2, are characterized by a DSL domain and tandem EGF-like repeats within the extracellular domain. The extracellular domain of the Notch receptor interacts with that of its ligands, typically on adjacent cells, resulting in two proteolytic cleaveages of Notch, an extracellular cleavage mediated by an ADAM protease and a cleavage within the transmembrane domain mediated by gamma secretase. This latter cleavage generates the Notch intracellular domain (NICD). The NICD then enters the nucleus where it activates the CBF1, Suppressor of Hairless [Su(H)], Lag-2 (CSL) family of transcription factors as the major downstream effectors to increase transcription of nuclear basic helix-loop-helix transcription factors of the Hairy and Enhancer of Split [E(spl)] family (Artavanis et al., 1999, *Science* 284:770; Brennan and Brown, 2003, *Breast Cancer Res.* 5:69; Iso et al., 2003, *Arterioscler. Thromb. Vasc. Biol.* 23:543). Alternative intracellular pathways involving the cytoplasmic protein Deltex identified in *Drosophila* may also exist in mammals (Martinez et al., 2002, *Curr. Opin. Genet. Dev.* 12:524-33), and this Deltex-dependent pathway may act to suppress expression of Wnt target genes (Brennan et al., 1999, *Curr. Biol.* 9:707-710; Lawrence et al., 2001, *Curr. Biol.* 11:375-85).

Jagged-1 is a type I, membrane-anchored, multidomain protein. It contains 26 exons that encode a polypeptide of approximately 1216 amino acids. The extracellular part of Jagged-1 is made up of a DSL domain, followed by a series of 16 EGF-like repeats, and a cysteine-rich region. Representative human Jagged-1 sequences include, but are not limited to Genbank accession nos. AAC52020 and U73936. The Jagged-1 DSL domain is located from about amino acids 167-229. The EGF-like repeats are located from about amino acids 230-856 and the cysteine rich region is located from about amino acids 863-930.

Hematopoietic stem cells (HSCs) are the best understood stem cells in the body, and Notch signaling is implicated both in their normal maintenance as well as in leukemic transformation (Kopper & Hajdu, 2004, *Pathol. Oncol. Res.* 10:69-73). HSCs are a rare population of cells that reside in a stomal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitor cells establishes immortalized cell lines that generate both lymphoid and myeloid cells in vitro and in long-term reconstitution assays (Vamum-Finney et al., 2000, *Nat. Med.* 6:1278-81), and the presence of Jagged 1 increases engraftment of human bone marrow cell populations enriched for HSCs (Karanu et al., 2000, *J. Exp. Med.* 192:1365-72). More recently, Notch signaling has been demonstrated in HSCs in vivo and shown to be involved in inhibiting HSC differentiation. Furthermore, Notch signaling appears to be required for Wnt-mediated HSC self-renewal (Duncan et al., 2005, *Nat. Immunol.* 6:314).

The Notch signaling pathway also plays a central role in the maintenance of neural stem cells and is implicated both in their normal maintenance as well as in brain cancers (Kopper & Hajdu, 2004, *Pathol. Oncol. Res.* 10:69-73; Purow et al., 2005, *Cancer Res.* 65:2353-63; Hallahan et al., 2004, *Cancer Res.* 64:7794-800). Neural stem cells give rise to all neuronal and glial cells in the mammalian nervous system during development, and more recently have been identified in the adult brain (Gage, 2000, *Science* 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS1 heterozygote mice (Nakamura et al., 2000, *J. Neurosci.* 20:283-93; Hitoshi et al., 2002, *Genes Dev.* 16:846-58). The reduction in neural stem cells appears to result from their premature differentiation into neurons (Hatakeyama et al., 2004, *Dev.* 131:5539-50) suggesting that Notch signaling regulates neural stem cell differentiation and self-renewal.

Aberrant Notch signaling is implicated in a number of human cancers. The NOTCH1 gene in humans was first identified in a subset of T-cell acute lymphoblastic leukemias as a translocated locus resulting in activation of the Notch pathway (Ellisen et al., 1991, *Cell* 66:649-61). Constitutive activation of Notch1 signaling in T-cells in mouse models similarly generates T-cell lymphomas suggesting a causative role (Robey et al., 1996, *Cell* 87:483-92; Pear et al., 1996, *J. Exp. Med.* 183:2283-91; Yan et al., 2001, *Blood* 98:3793-9; Bellavia et al., 2000, *EMBO J.* 19:3337-48). Recently NOTCH1 point mutations, insertions, and deletions producing aberrant NOTCH1 signaling have been found to be frequently present in both childhood and adult T-cell acute lymphoblastic leukemia/lymphoma (Pear & Aster, 2004, *Curr. Opin. Hematol.* 11:416-33).

The frequent insertion of the mouse mammary tumor virus into both the Notch1 and Notch4 locus in mammary tumors and the resulting activated Notch protein fragments first implicated Notch signaling in breast cancer (Gallahan & Callahan, 1987, *J. Virol.* 61:66-74; Brennan & Brown, 2003, *Breast Cancer Res.* 5:69; Politi et al., 2004, *Semin. Cancer Biol.* 14:341-7). Further studies in transgenic mice have confirmed a role for Notch in ductal branching during normal mammary gland development, and a constitutively active form of Notch4 in mammary epithelial cells inhibits epithelial differentiation and results in tumorigenesis (Jhappan et al., 1992, *Genes & Dev.* 6:345-5; Gallahan et al., 1996, *Cancer Res.* 56:1775-85; Smith et al., 1995, *Cell Growth Differ.* 6:563-77; Soriano et al., 2000, *Int. J. Cancer* 86:652-9; Uyttendaele et al., 1998, *Dev. Biol.* 196:204-17; Politi et al., 2004, *Semin. Cancer Biol.* 14:341-7). Currently the evidence for a role for Notch in human breast cancer is limited to the expression of Notch receptors in breast carcinomas and their correlation with clinical outcome (Weijzen et al., 2002, *Nat. Med.* 8:979-86; Parr et al., 2004, *Int. J. Mol. Med.* 14:779-86). Furthermore, overexpression of the Notch pathway has been observed in cervical cancers (Zagouras et al., 1995, *PNAS* 92:6414-8), renal cell carcinomas (Rae et al., 2000, *Int. J. Cancer* 88:726-32), head and neck squamous cell carcinomas (Leethanakul et al., 2000, *Oncogene* 19:3220-4), endometrial cancers (Suzuki et al., 2000, *Int. J. Oncol.* 17:1131-9), and neuroblastomas (van Limpt et al., 2000, *Med. Pediatr. Oncol.* 35:554-8) indicative of a potential role for Notch in the development of a number of neoplasms. Interestingly, Notch signaling might play a role in the maintenance of the undifferentiated state of Apc-mutant neoplastic cells of the colon (van Es & Clevers, 2005, *Trends Mol. Med.* 11:496-502).

The Notch pathway is also involved in multiple aspects of vascular development including proliferation, migration, smooth muscle differentiation, angiogenesis and arterial-venous differentiation (Iso et al., 2003, *Arterioscler. Thromb. Vasc. Biol.* 23:543).

For example, homozygous null mutations in Notch-¼ and Jagged-1 as well as heterozygous loss of Dll4 result in severe though variable defects in arterial development and yolk sac vascularization. Furthermore, Dll1-deficient and Notch-2-hypomorphic mice embryos show hemorrhage that likely results from poor development of vascular structures (Gale et al., 2004, *PNAS*, 101:15949-54; Krebs et al., 2000, *Genes Dev.* 14:1343-52; Xue et al., 1999, *Hum. Mel Genet.* 8:723-30; Hrabe de Angelis et al., 1997, *Nature* 386:717-21; McCright et al., 2001, *Dev.* 128:491-502). In humans, mutations in JAGGED 1 are associated with Alagille syndrome, a developmental disorder that includes vascular defects, and mutations in NOTCH3 are responsible for an inherited vascular dementia (CADASIL) in which vessel homeostasis is defective (Joutel et al., 1996, *Nature* 383:707-10).

The identification of Jagged 1 as expressed in cancer stem cells compared to normal breast epithelium suggested targeting the Notch pathway to eliminate not only the majority of non-tumorigenic cancer cells, but the tumorigenic cells responsible for the formation and reoccurrence of solid tumors. Furthermore, because of the prominent role of angiogenesis in tumor formation and maintenance, targeting the Notch pathway can also effectively inhibit angiogenesis, starving a cancer of nutrients and contributing to its elimination.

Thus, present invention provides a cancer stem cell marker, the expression of which can be analyzed to diagnosis or monitor a disease associated with cancer. In some embodiments, expression of a cancer stem cell marker is determined by polynucleotide expression such as, for example, mRNA encoding the cancer stem cell marker. The polynucleotide can be detected and quantified by any of a number of means well known to those of skill in the art. In some embodiments, mRNA encoding a cancer stem cell marker is detected by in situ hybridization of tissue sections from, for example, a patient biopsy. In some embodiments, RNA is isolated from a tissue and detected by, for example, Northern blot, quantitative RT-PCR, or microarrays. For example, total RNA can be extracted from a tissue sample and primers that specifically hybridize and amplify a cancer stem cell marker can be used to detect expression of a cancer stem cell marker polynucleotide using RT-PCR.

In certain embodiments, expression of a cancer stem cell marker can be determined by detection of the corresponding polypeptide. The polypeptide can be detected and quantified by any of a number of means well known. In some embodiments, a cancer stem cell marker polypeptide is detected using analytic biochemical methods such as, for example, electrophoresis, capillary electrophoresis, high performance liquid chromatography (HPLC) or thin layer chromatography (TLC). The isolated polypeptide can also be sequenced according to standard techniques. In some embodiments, a cancer stem cell marker protein is detected with antibodies raised against the protein using, for example, immunofluorescence or immunohistochemistry on tissue sections. Alternatively antibodies against a cancer stem cell marker can detect expression using, for example, ELISA, FACS, Western blot, immunoprecipitation or protein microarrays. For example, cancer stem cells can be isolated from a patient biopsy and expression of a cancer stem cell marker protein detected with fluorescently labeled antibodies using FACS. In another method, the cells expressing a cancer stem cell marker can be detected in vivo using labeled antibodies in typical imaging system. For example, antibodies labeled with paramagnetic isotopes can be used for magnetic resonance imaging (MRI).

In some embodiments of the present invention, a diagnostic assay comprises determining the expression or not of a cancer stem cell marker in tumor cells using, for example, immunohistochemistry, in situ hybridization, or RT-PCR. In other embodiments, a diagnostic assay comprises determining expression levels of a cancer stem cell marker using, for example, quantitative RT-PCR. In some embodiments, a diagnostic assay further comprises determining expression levels of a cancer stem cell marker compared to a control tissue such as, for example, normal epithelium.

Detection of a cancer stem cell marker expression can then be used to provide a prognosis and select a therapy. A prognosis can be based on any known risk expression of a cancer stem cell marker indicates. Furthermore, detection of a cancer stem cell marker can be used to select an appropriate therapy including, for example, treatment with antibodies against the detected cancer stem cell marker protein. In certain embodiments, the antibody specifically binds to the extracellular domain of a cancer stem cell marker protein such as the Notch receptor ligand, Jagged 1.

In the context of the present invention, a suitable antibody is an agent that can have one or more of the following effects, for example: interfere with the expression of a cancer stem cell marker; interfere with activation of a cancer stem cell signal transduction pathway by, for example, sterically inhibiting interactions between a cancer stem cell marker and its ligand, receptor or co-receptors; activate a cancer stem cell signal transduction pathway by, for example, acting as a ligand or promoting the binding of an endogenous ligand; or bind to a cancer stem cell marker and inhibit tumor cell proliferation.

In certain embodiments, antibodies against a cancer stem cell marker act extracellularly to modulate the function of a cancer stem cell marker protein. In some embodiments, extracellular binding of an antibody against a cancer stem cell marker can inhibit the signaling of a cancer stem cell marker protein by, for example, inhibiting intrinsic activation (e.g. kinase activity) of a cancer stem cell marker and/or by sterically inhibiting the interaction, for example, of a cancer stem cell marker with its ligand, with its receptor, with a co-receptor, or with the extracellular matrix. In some embodiments, extracellular binding of an antibody against a cancer stem cell marker can down-regulate cell-surface expression of a cancer stem cell marker such as, for example, by internalization of a cancer stem cell marker protein or decreasing cell surface trafficking of a cancer stem cell marker. In some embodiments, extracellular binding of an antibody against a cancer stem cell marker can promote the signaling of a cancer stem cell marker protein by, for example, acting as a decoy ligand or increasing ligand binding.

In certain embodiments, antibodies against a cancer stem cell marker bind to a cancer stem cell marker protein and have one or more of the following effects: inhibit proliferation of tumor cells, trigger cell death of tumor cells, or prevent metastasis of tumor cells. In certain embodiments, antibodies against a cancer stem cell marker trigger cell death via a conjugated toxin, chemotherapeutic agent, radioisotope, or other such agent. For example, an antibody against a cancer stem cell marker is conjugated to a toxin that is activated in tumor cells expressing the cancer stem cell marker by protein internalization.

In certain embodiments, antibodies against a cancer stem cell marker mediate cell death of a cell expressing the cancer stem cell marker protein via antibody-dependent cellular cytotoxicity (ADCC). ADCC involves cell lysis by effector cells that recognize the Fc portion of an antibody. Many lymphocytes, monocytes, tissue macrophages, granulocytes and eosinophiles, for example, have Fc receptors and can mediate cytolysis (Dillman, 1994, *J. Clin. Oncol.* 12:1497).

In certain embodiments, antibodies against a cancer stem cell marker trigger cell death of a cell expressing a cancer stem cell marker protein by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity are prepared.

The ability of any particular antibody against a cancer stem cell to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, antibodies against a cancer stem cell marker can trigger cell death inhibiting angiogenesis. Angiogenesis is the process by which new blood vessels form from pre-existing vessels and is a fundamental process required for normal growth, for example, during embryonic development, wound healing, and in response to ovulation. Solid tumor growth larger than 1-2 mm$^2$ also requires angiogenesis to supply nutrients and oxygen without which tumor cells die. In certain embodiments, an antibody against a cancer stem cell marker targets vascular cells that express the cancer stem cell marker including, for example, endothelial cells, smooth muscle cells, or components of the extracellular matrix required for vascular assembly. In certain embodiments, an antibody against a cancer stem cell marker inhibits growth factor signaling required by vascular cell recruitment, assembly, maintenance, or survival.

The antibodies against a cancer stem cell marker find use in the diagnostic and therapeutic methods described herein. In certain embodiments, the antibodies of the present invention are used to detect the expression of a cancer stem cell marker protein in biological samples such as, for example, a patient tissue biopsy, pleural effusion, or blood sample. Tissue biopsies can be sectioned and protein detected using, for example, immunofluorescence or immunohistochemistry. In addition, individual cells from a sample can be isolated, and protein expression detected on fixed or live cells by FACS analysis. In certain embodiments, antibodies can be used on protein arrays to detect expression of a cancer stem cell marker, for example, on tumor cells, in cell lysates, or in other protein samples. In certain embodiments, the antibodies of the present invention are used to inhibit the growth of tumor cells by contacting the antibodies with tumor cells in in vitro cell based assays, in vivo animal models, etc. In certain embodiments, the antibodies are used to treat cancer in a patient by administering a therapeutically effective amount of an antibody against a cancer stem cell marker.

The antibodies of the invention can be prepared by any conventional means known in the art. For example, polyclonal antibodies can be prepared by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) *Nature* 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro.

Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, *Nature*, 348:552-554; Clackson et al., 1991, *Nature*, 352:624-628; and Marks et al., 1991, *J. Mol. Biol.*, 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments of the present invention, the monoclonal antibody against a cancer stem cell marker is a humanized antibody. Humanized antibodies are antibodies that contain minimal sequences from non-human (e.g murine) antibodies within the variable regions. Such antibodies are used therapeutically to reduce antigenicity and HAMA (human anti-mouse antibody) responses when administered to a human subject.

In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDRs of a human antibody with those of a non-human antibody (e.g. mouse, rat, rabbit, hamster, etc.) having the desired specificity, affinity, and capability following the methods of Jones et al., 1986, *Nature*, 321:522-525; Riechmann et al., 1988, *Nature*, 332:323-327; Verhoeyen et al., 1988, *Science*, 239:1534-1536. The humanized antibody can be further modified by the substitution of additional residue either in the variable human framework region and/or within the replaced non-human residues to refine and optimize antibody specificity, affinity, and/or capability.

The choice of human heavy and/or light chain variable domains to be used in making humanized antibodies can be important for reducing antigenicity. According to the "best-fit" method, the sequence of the variable domain of a rodent antibody is screened against the entire library of known human variable-domain amino acid sequences. Thus in certain embodiments, the human amino acid sequence which is most homologous to that of the rodent antibody from which the CDRs are taken is used as the human framework region (FR) for the humanized antibody (Sims et al., 1993, *J. Immunol,* 151: 2296; Chothia et al., 1987, *J. Mol. Biol.,* 196: 901). Another method uses a particular FR derived from the consensus sequence of all human antibodies of a particular subgroup of light or heavy chains and can be used for several difference humanized antibodies (Carter et al., 1992, *PNAS,* 89; 4285; Presta et al., 1993, *J. Immunol,* 151: 2623). In certain embodiments, a combination of methods is used to pick the human variable FR to use in generation of humanized antibodies.

It is further understood that antibodies (e.g. rodent) to be humanized must retain high affinity for the antigen as well as other favorable biological properties. To achieve this goal, humanized antibodies can be prepared by a process of analysis of the parental sequence from the rodent antibody to be humanized and the various candidate humanizing sequences. Three-dimensional immunoglobulin models are available. Computer programs can be used to illustrate and display probable three-dimensional conformational structures of selected candidate antibody sequences. Use of such models permits analysis of the likely role of the residues in the function of the antibody to be humanized, i.e., the analysis of residues that influence the ability of the candidate antibody to bind its antigen. In this way, FR residues can be selected and combined from the parental antibody to the recipient humanized antibody so that the desired antibody characteristics are achieved. In general, the residues in the CDRs of the antigen determination region (or hypervariable region) are retained from the parental antibody (e.g. the rodent antibody with the desired antigen binding properties) in the humanized antibody for antigen binding. In certain embodiments, at least one additional residue within the variable FR is retained from the parental antibody in the humanized antibody. In certain embodiments, up to six additional residues within the variable FR are retained from the parental antibody in the humanized antibody.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest, U.S. Department of Health and Human Services, 1987, 1991. Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Moreover, any two antibody sequences can be uniquely aligned, for example to determine percent identity, by using the Kabat numbering system so that each amino acid in one antibody sequence is aligned with the amino acid in the other sequence that has the same Kabat number. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

In addition, fully human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, *J. Immunol.,* 147 (1):86-95; and U.S. Pat. No. 5,750,373). Also, the human antibody can be selected from a phage library, where that phage library expresses human antibodies (Vaughan et al., 1996, *Nat. Biotech.,* 14:309-314; Sheets et al., 1998, *Proc. Nat'l. Acad. Sci.,* 95:6157-6162; Hoogenboom and Winter, 1991, *J. Mol. Biol.,* 227:381; Marks et al., 1991, *J. Mol. Biol.,* 222:581). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a cancer stem cell marker. Bispecific antibodies are antibodies that are capable of specifically recognizing and binding at least two different epitopes. The different epitopes can either be within the same molecule (e.g. the same cancer stem cell marker polypeptide) or on different molecules such that both, for example, the antibodies can specifically recognize and bind a cancer stem cell marker as well as, for example, 1) an effector molecule on a leukocyte such as a T-cell receptor (e.g. CD3) or Fc receptor (e.g. CD64, CD32, or CD16) or 2) a cytotoxic agent as described in detail below. Bispecific antibodies can be intact antibodies or antibody fragments.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, *Nature* 305:537-539; Brennan et al., 1985, *Science* 229:81; Suresh et al, 1986, *Methods in Enzymol.* 121:120; Traunecker et al., 1991, *EMBO J.* 10:3655-3659; Shalaby et al., 1992, *J. Exp. Med.* 175:217-225; Kostelny et al., 1992, *J. Immunol.* 148:

1547-1553; Gruber et al., 1994, *J. Immunol.* 152:5368; and U.S. Pat. No. 5,731,168). Antibodies with more than two valencies are also contemplated. For example, trispecific antibodies can be prepared (Tutt et al., *J. Immunol.* 147:60 (1991)).

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, *Journal of Biochemical and Biophysical Methods* 24:107-117; Brennan et al., 1985, *Science,* 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to a polypeptide of the invention (see U.S. Pat. No. 4,946,778). In addition, methods can be adapted for the construction of Fab expression libraries (Huse, et al., *Science* 246:1275-1281 (1989)) to allow rapid and effective identification of monoclonal Fab fragments with the desired specificity for the Notch receptor ligand DLL4, or derivatives, fragments, or homologs thereof. Antibody fragments that contain the idiotypes to a polypeptide of the invention may be produced by techniques in the art including, but not limited to: (a) an F(ab')2 fragment produced by pepsin digestion of an antibody molecule; (b) an Fab fragment generated by reducing the disulfide bridges of an F(ab')2 fragment, (c) an Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of human Jagged 1. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

The variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In some embodiments the modified antibodies will comprise domain deleted constructs or variants wherein the entire CH2 domain has been removed ($\Delta$CH2 constructs). In some embodiments the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques well within the purview of the skilled artisan.

It will be noted that the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, any spacer added to the construct be relatively non-immunogenic or, even omitted altogether if the desired biochemical qualities of the modified antibodies may be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. In some embodiments, the antibodies can be conjugated to radioisotopes, such as $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of well known chelators or direct labeling. In other embodiments, the disclosed compositions can comprise antibodies coupled to drugs, prodrugs or lymphokines such as interferon. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used. In some embodiments, the modified antibodies can be complexed with other immunologically active ligands (e.g. antibodies or fragments thereof) wherein the resulting molecule binds to both the neoplastic cell and an effector cell such as a T cell.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. The selection of which conjugated or unconjugated modified antibody to use will depend of the type and stage of cancer, use of adjunct treatment (e.g., chemotherapy or external radiation) and patient condition. It will be appreciated that one skilled in the art could readily make such a selection in view of the teachings herein.

The antibodies of the present invention can be assayed for immunospecific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In some embodiments, the immunospecificity of an antibody against a cancer stem cell marker is determined using ELISA. An ELISA assay comprises preparing antigen, coating wells of a 96 well microtiter plate with antigen, adding the antibody against a cancer stem cell marker conjugated to a detectable compound such as an enzymatic substrate (e.g. horseradish peroxidase or alkaline phosphatase) to the well, incubating for a period of time and detecting the presence of the antigen. In some embodiments, the antibody against a cancer stem cell marker is not conjugated to a detectable compound, but instead a second conjugated antibody that recognizes the antibody against a cancer stem cell marker is added to the well. In some embodiments, instead of coating the well with the antigen, the antibody against a cancer stem cell marker can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of an antibody to a cancer stem cell marker antigen and the off-rate of an antibody-antigen interaction can be determined by competitive binding assays. One example of a competitive binding assay is a radioimmunoassay comprising the incubation of labeled antigen (e.g. $^3$H or $^{125}$I), or fragment or variant thereof, with the antibody of interest in the presence of increasing amounts of unlabeled antigen followed by the detection of the antibody bound to the labeled antigen. The affinity of the antibody against a cancer stem cell marker and the binding off-rates can be determined from the data by scatchard plot analysis. In some embodiments, BIAcore kinetic analysis is used to determine the binding on and off rates of antibodies against a cancer stem cell marker. BIAcore kinetic analysis comprises analyzing the binding and dissociation of antibodies from chips with immobilized cancer stem cell marker antigens on their surface.

In certain embodiments, the invention encompasses isolated polynucleotides that encode a polypeptide comprising an antibody, or fragment thereof, against human Jagged 1.

Thus, the term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The present invention further relates to variants of the hereinabove described polynucleotides encoding, for example, fragments, analogs, and derivatives. The variant of the polynucleotide can be a naturally occurring allelic variant of the polynucleotide or a non-naturally occurring variant of the polynucleotide. In certain embodiments, the polynucleotide can have a coding sequence which is a naturally occurring allelic variant of the coding sequence of the disclosed polypeptides. As known in the art, an allelic variant is an alternate form of a polynucleotide sequence that have, for example, a substitution, deletion, or addition of one or more nucleotides, which does not substantially alter the function of the encoded polypeptide.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

In certain embodiments, the present invention provides isolated nucleic acid molecules having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, against human Jagged 1.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The polypeptides of the present invention can be recombinant polypeptides, natural polypeptides, or synthetic polypeptides comprising an antibody, or fragment thereof, against human Jagged 1. It will be recognized in the art that some amino acid sequences of the invention can be varied without significant effect of the structure or function of the protein. Thus, the invention further includes variations of the polypeptides which show substantial activity or which include regions of an antibody, or fragment thereof, against human Jagged 1 protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., *Proc. Nat'l. Acad. Sci. USA* 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

Recombinant expression vectors are used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a cancer stem cell marker protein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

The present invention provides methods for inhibiting the growth of tumorigenic cells expressing a cancer stem cell marker using the antibodies against a cancer stem cell marker described herein. In certain embodiments, the method of inhibiting the growth of tumorigenic cells expressing a cancer stem cell marker comprises contacting the cell with an antibody against a cancer stem cell marker in vitro. For example, an immortalized cell line or a cancer cell line that expresses a cancer stem cell marker is cultured in medium to which is added an antibody against the expressed cancer stem cell marker to inhibit cell growth. In some embodiments, tumor cells comprising tumor stem cells are isolated from a patient sample such as, for example, a tissue biopsy, pleural effusion, or blood sample and cultured in medium to which is added an antibody against a cancer stem cell marker to inhibit cell growth.

In some embodiments, the method of inhibiting the growth of tumorigenic cells expressing a cancer stem cell marker comprises contacting the cell with an antibody against a cancer stem cell marker in vivo. In certain embodiments, contacting a tumorigenic cell with an antibody against a cancer stem cell marker is undertaken in an animal model. For example, xenografts expressing a cancer stem cell marker are grown in immunocompromised mice (e.g. NOD/SCID mice) that are administered an antibody against a cancer stem cell marker to inhibit tumor growth. In some embodiments, cancer stem cells that express a cancer stem cell marker are isolated from a patient sample such as, for example, a tissue biopsy, pleural effusion, or blood sample and injected into immunocompromised mice that are then administered an antibody against the cancer stem cell marker to inhibit tumor cell growth. In some embodiments, the antibody against a cancer stem cell marker is administered at the same time or shortly after introduction of tumorigenic cells into the animal to prevent tumor growth. In some embodiments, the antibody against a cancer stem cell marker is administered as a therapeutic after the tumorigenic cells have grown to a specified size.

The present invention further provides pharmaceutical compositions comprising antibodies that target a cancer stem cell marker. These pharmaceutical compositions find use in inhibiting tumor cell growth and treating cancer in human patients.

Formulations are prepared for storage and use by combining a purified antibody of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration. The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antibodies of the present invention complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antibodies can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the treatment involves the combined administration of an antibody of the present invention and a chemotherapeutic agent or cocktail of multiple different chemotherapeutic agents. Treatment with an antibody can occur prior to, concurrently with, or subsequent to administration of chemotherapies. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In other embodiments, the treatment involves the combined administration of an antibody of the present invention and radiation therapy. Treatment with the antibody can occur prior to, concurrently with, or subsequent to administration of radiation therapy.

Any dosing schedules for such radiation therapy can be used as determined by the skilled practitioner.

In other embodiments, the treatment can involve the combined administration of antibodies of the present invention with other antibodies against additional tumor associated antigens including, but not limited to, antibodies that bind to the EGF receptor (EGFR) (Erbitux®), the erbB2 receptor (HER2) (Herceptin®), and vascular endothelial growth factor (VEGF) (Avastin®). Furthermore, treatment can include administration of one or more cytokines, can be accompanied by surgical removal of cancer cells or any other therapy deemed necessary by a treating physician.

For the treatment of the disease, the appropriate dosage of an antibody of the present invention depends on the type of disease to be treated, the severity and course of the disease, the responsiveness of the disease, whether the antibody is administered for therapeutic or preventative purposes, previous therapy, patient's clinical history, and so on all at the discretion of the treating physician. The antibody can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the antibodies described herein and that can be used to perform the methods described herein. In certain embodiments, a kit comprises at least one purified antibody against a cancer stem cell marker in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies of the present invention can be readily incorporated into one of the established kit formats which are well known in the art.

Embodiments of the present disclosure can be further defined by reference to the following examples, which describe in detail preparation of antibodies of the present disclosure and methods for using antibodies of the present disclosure. Many modifications, both to materials and methods, may be practiced without departing from the scope of the present disclosure. Wherever possible, the same reference numbers will be used throughout the drawings to refer to the same or like parts. As used herein and in the appended claims, the singular forms "a," "or," and "the" include plural referents unless the context clearly dictates otherwise. Thus, for example, reference to "an antibody" includes a plurality of such antibodies or one or more antibodies and equivalents thereof known to those skilled in the art. Furthermore, all numbers expressing quantities of ingredients, reaction conditions, purity, polypeptide and polynucleotide lengths, and so forth, used in the specification, are modified by the term "about," unless otherwise indicated. Accordingly, the numerical parameters set forth in the specification and claims are approximations that may vary depending upon the desired properties of the present invention.

EXAMPLES

Example 1

Production of Jagged 1 Antibodies

Antigen Production

A recombinant polypeptide fragment of the extracellular domain of human Jagged 1 was generated as an antigen for antibody production. Standard recombinant DNA technology was used to isolate a polynucleotide encoding amino acids 1-1060 of Jagged 1. This polynucleotide was ligated in-frame N-terminal to either a human Fc-tag or histidine-tag and cloned into a transfer plasmid vector for baculovirus mediated expression in insect cells. Standard transfection, infection, and cell culture protocols were used to produce recombinant insect cells expressing the corresponding Jagged 1 polypeptide (O'Reilley et al., *Baculovirus expression vectors: A Laboratory Manual* Oxford: Oxford University Press (1994)).

Cleavage of the endogenous signal sequence of human Jagged 1 was approximated using cleavage prediction software SignalP 3.0, however the actual in vivo cleavage point can differ by a couple of amino acids either direction. The predicted cleavage of Jagged 1 is between amino acids 1 and 23, thus Jagged 1 antigen protein comprises approximately amino acid 24 through amino acid 1060. Antigen protein was purified from insect cell conditioned medium using Protein A and $Ni^{++}$-chelate affinity chromatography. Purified antigen protein was then dialyzed against PBS (pH=7), concentrated to approximately 1 mg/ml, and sterile filtered in preparation for immunization.

Immunization

Mice (n=3) were immunized with purified Jagged 1 antigen protein (Antibody Solutions; Mountain View, Calif.) using standard techniques. Blood from individual mice was screened approximately 70 days after initial immunization for antigen recognition using ELISA and FACS analysis (described in detail below). The two animals with the highest antibody titers were selected for final antigen boost after which spleen cells were isolated for hybridoma production. Hybridoma cells were plated at 1 cell per well in 96 well plates, and the supernatant from each well screened by ELISA and FACS analysis against antigen protein. Several hybridomas with high antibody titer were selected and scaled up in static flask culture. Antibodies were purified from the hybridoma supernatant using protein A or protein G agarose chromatography. Purified monoclonal antibodies are again tested by FACS and are isotyped to select for IgG and IgM antibodies. Anti-Jagged 1 antibodies 64M6, 64M7, 64M12, 64M14, and 64M23 were tested further. Antibody 64M14 was deposited on Oct. 15, 2009 under the terms of the Budapest Treaty with American Type Culture Collection (ATCC), located at 10801 University Blvd., Manassas, Va. 20110-2209) and given deposit number PTA-10416.

FACS Analysis

To select monoclonal antibodies produced by hybridomas clones that recognize native cell-surface Jagged 1 protein, FACs analysis is used. HEK293 cells are co-transfected with expression vectors encoding a full-length cDNA clone of Jagged 1 and the transfection marker GFP. Twenty-four to forty-eight hours post-transfection, cells were collected in suspension and incubated on ice with anti-Jagged 1 antibodies or control IgG to detect background antibody binding. The cells are washed and primary antibodies detected with anti-mouse secondary antibodies conjugated to a fluorescent chromophore. Labeled cells are then sorted by FACS to identify anti-Jagged 1 antibodies that specifically recognize cell surface expression of native cell-surface Jagged 1 protein.

Epitope Mapping

To identify antibodies that recognize specific regions of the Jagged 1 extracellular domain, epitope mapping was performed. Mammalian expression plasmid vectors comprising a CMV promoter upstream of polynucleotides that encode a series of deletion fragments of the extracellular domain of Jagged 1 fused to Fc protein were generated using standard recombinant DNA technology. These recombinant fusion proteins were expressed in transiently transfected HEK 293 cells from which conditioned medium was collected twenty-four to forty-eight hours post-transfection and cell lysate protein separated on non-reducing SDS-PAGE acrylamide gels for Western blotting. As shown in FIG. 1, anti-Jagged 1 64M6, 64M7, 64M12, 64M14, and 64M23 antibodies bind to EGF1 (FIG. 1).

To identify more specifically epitopes within the extracellular domains recognized by an antibody against DLL4 the SPOTs system is used (Sigma Genosys, The Woodlands, Tex.). A series of 10-residue linear peptides overlapping by one amino acid and covering the entire DLL4 extracellular domain are synthesized and covalently bound to a cellulose membrane by the SPOT synthesis technique. The membrane is pre-incubated for eight hours at room temperature with blocking buffer and hybridized with antibody overnight at 4° C. The membrane is then washed, incubated with a secondary antibody conjugated to horseradish peroxidase (HRP) (Amersham Bioscience, Piscataway, N.J.), re-washed, and visualized with signal development solution containing 3-amino-9-ethylcarbazole. Specific epitopes recognized by an antibody are thus determined.

Example 2

Chimeric Antibodies

After monoclonal antibodies that specifically recognize Jagged 1 are identified, these antibodies are modified to overcome the human anti-mouse antibody (HAMA) immune response when rodent antibodies are used as therapeutics agents. In certain embodiments, the variable regions of the heavy-chain and light-chain of the selected monoclonal antibody are isolated by RT-PCR from hybridoma cells and ligated in-frame to human $IgG_1$ heavy-chain and kappa light chain constant regions, respectively, in mammalian expression vectors. Alternatively a human Ig expression vector such as TCAE 5.3 is used that contains the human $IgG_1$ heavy-chain and kappa light-chain constant region genes on the same plasmid (Preston et al., 1998, *Infection & Immunity* 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against Jagged 1 can undergo further humanization. To generate humanized antibodies the three short hypervariable sequences, or complementary determining regions (CDRs), of the chimeric antibody heavy- and light-chain variable domains described above are engineered using recombinant DNA technology into the variable domain framework of a human heavy- and light-chain sequences, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Human Antibodies

In some embodiments, human antibodies that specifically recognize the extracellular domain of Jagged 1 are isolated using phage display technology. A synthetic antibody library containing human antibody variable domains is screened for specific and high affinity recognition of the Jagged 1 antigen described above. CDR cassettes in the library are specifically exchanged via unique flanking restriction sites for antibody optimization. Optimized human variable regions are then cloned into an Ig expression vector containing human $IgG_1$ heavy-chain and kappa light-chain for expression of human antibodies in mammalian cells.

Example 3

In Vitro Assays to Evaluate Antibodies Against Jagged 1

This example describes representative in vitro assays to test the activity of antibodies generated against Jagged 1 on Notch binding and endothelial cell sprouting.

Notch Receptor Binding

To determine the effect of anti-Jagged 1 antibodies on Jagged 1 ligand binding to Notch receptors, a FACS-based assay was used. Full-length human Notch 1 was stably expressed in HEK 293 cells, and the cells were incubated with fusion proteins containing the extracellular domain of either human or rat Jagged 1 fused to human Fc. Binding was detected by fluorescently labeled anti-human Fc in FACS binding assay. Anti-Jagged 1 64M14 antibodies inhibited binding of either human or rat Jagged 1 to Notch 1 (FIG. 2). In contrast, 64M12 had no effect on Jagged 1 binding to Notch 1 (FIG. 2).

Sprouting Assay

To determine the effect of anti-Jagged 1 monoclonal antibodies on endothelial cells, in vitro cell assays were used. Dextran-coated Cytodex 3 microcarrier beads (Amersham) were mixed with Human Blood Microvascular Endothelial Cells (HBMVECs, neonatal purchased from Cambrex) (400/bead) in EGM-2 (Cambrex) and incubated overnight at 37° C. Cell-coated beads were washed in PBS and resuspended in PBS with 2.5 mg/ml Fibrinogen (Sigma). Bead suspension (0.5 mL; 200 beads/mL) was added to each well of a 24-well plate containing 0.5U thrombin (Sigma) and incubated for 5 minutes at room temperature and 30 minutes at 37° C. The clot was equilibrated in EGM-2 medium by three changes of medium for 15 minutes each. The medium was replaced by addition of EGM-2 medium containing 20 thousand skin fibroblast cells (Detroit 551, ATCC). Dibenzazepine (DBZ; gamma-secretase inhibitor, 100 nM final concentration) or anti-Jagged 64M14 antibodies (20 ug/ml) were added to each well, and medium was changed every three days. The wells were monitored for six days and images of representative fields were captured (FIG. 3).

Anti-Jag1 antibody (64M14) caused enhanced sprouting of HBMVECs co-cultured with skin fibroblasts in fibrin gels, whereas addition of a control antibody (anti-trinitrophenol hapten) did not result in increased sprouting (FIG. 3). Similar increase in sprouting in fibrin was observed up treatment with a gamma-secretase inhibitor DBZ, demonstrating the involvement of Notch signaling in regulating endothelial cell sprouting processes (FIG. 3).

Example 4

In Vivo Treatment of Tumor Growth Using Anti-Jagged 1 Antibodies

This example describes the use of anti-Jagged 1 antibodies to prevent tumor growth in a xenograft model. In certain embodiments, tumor cells from a patient sample (solid tumor biopsy or pleural effusion) that have been passaged as a xenograft in mice are prepared for repassaging into experimental animals. Tumor tissue is removed under sterile conditions, cut up into small pieces, minced completely using sterile blades, and single cell suspensions obtained by enzymatic digestion and mechanical disruption. Specifically, pleural effusion cells or the resulting tumor pieces are mixed with ultra-pure collagenase III in culture medium (200-250 units of collagenase per mL) and incubated at 37° C. for 3-4 hours with pipetting up and down through a 10-mL pipette every 15-20 minutes. Digested cells are filtered through a 45 µM nylon mesh, washed with RPMI/20% FBS, and washed twice with HBSS. Dissociated tumor cells are then injected subcutaneously into the mammary fat pads of NOD/SCID mice to elicit tumor growth.

In certain embodiments, dissociated tumor cells are first sorted into tumorigenic and non-tumorigenic cells based on cell surface markers before injection into experimental animals. Specifically, tumor cells dissociated as described above are washed twice with Hepes buffered saline solution (HBSS) containing 2% heat-inactivated calf serum (HICS) and resuspended at $10^6$ cells per 100 µl. Antibodies are added and the cells incubated for 20 minutes on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD 16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2 Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24-/low, Lin-tumorigenic cells are then injected subcutaneously into NOD/SCID mice to elicit tumor growth.

Example 5

In certain embodiments, anti-Jagged 1 antibodies were analyzed for their ability to reduce the growth of UM-C17 colon tumor cells. Dissociated UM-C17 cells (10,000 per animal) were injected subcutaneously into the right flank region of 6-8 week old NOD/SCID mice. Day 19 after tumor cell injection, when tumors were approximately 100 mm³, animals were injected intraperitoneal (i.p.) with either 10 mg/kg 64M14 anti-Jagged 1 antibodies, 10 mg/kg 64M14 anti-Jagged 1 antibody and 10 mg/kg Avastin (anti-VEGF), Avastin alone, or control antibody anti-DNP (dinitrophenol or anti-hapten) (n=10 per group) two times per week for the duration of the experiment. Both treatment with 64M14 antibodies and Avastin reduced tumor growth by close to 50% compared to controls (FIG. 4). The combination therapy reduced tumor growth better than either antibody alone (FIG. 4).

Example 6

Treatment of Human Cancer Using Humanized Anti-Jagged 1 Antibodies

This example describes methods for treating cancer using monoclonal antibodies against Jagged 1 to target tumors comprising cancer stem cells and/or tumor cells in which Notch receptor or Notch receptor ligand expression has been detected. The presence of cancer stem cell marker expression can first be determined from a tumor biopsy. Tumor cells from a biopsy from a patient diagnosed with cancer are removed under sterile conditions. In some embodiments the tissue biopsy is fresh-frozen in liquid nitrogen, embedded in O.C.T., and cut on a cryostat as 10 µm sections onto glass slides.

In some embodiments, the tissue biopsy is formalin-fixed, paraffin-embedded, and cut on a microtome as 10 µm section onto glass slides. Sections are incubated with antibodies against Jagged 1 to detect protein expression.

The presence of cancer stem cells can also be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -JAG1 antibodies to detect cancer stem cells, and the presence of ESA+, CD44+, CD24-/low, Lin-, JAG1+ tumor stem cells is determined by flow cytometry as described in detail above.

Cancer patients whose tumors are diagnosed as expressing a Notch receptor or Notch receptor ligand are treated with humanized anti-Jagged 1 antibodies. In certain embodiments, humanized anti-Jagged 1 antibodies generated as described above are purified and formulated with a suitable pharmaceutical vehicle for injection. In some embodiments, patients are treated with the Jagged 1 antibodies at least once a month for at least 10 weeks. In some embodiments, patients are treated with the Jagged 1 antibodies at least once a week for at least about 14 weeks. Each administration of the antibody should be a pharmaceutically effective dose. In some embodiments, between about 2 to about 100 mg/ml of an anti-Jagged 1 antibody is administered. In some embodiments, between about 5 to about 40 mg/ml of an anti-Jagged 1 antibody is administered. The antibody can be administered prior to, concurrently with, or after standard radiotherapy regimens or chemotherapy regimens using one or more chemotherapeutic agent, such as oxaliplatin, fluorouracil, leucovorin, or streptozocin. The antibody can be administered prior to, concurrently with, or after antibody treatment, including treatment with Avastin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

Other embodiments of the invention will be apparent from consideration of the specification and practice of the invention disclosed herein. It is intended that the specification and examples be considered as exemplary only, with a true scope and spirit of the invention being indicated by the following claims.

What is claimed is:

1. An isolated monoclonal antibody that competes for specific binding to human Jagged 1 with the antibody 64M14.
2. The antibody of claim 1 which is a chimeric antibody.
3. The antibody of claim 1 which is a humanized antibody.
4. The antibody of claim 1 which is a human antibody.
5. A composition comprising the monoclonal antibody of claim 1.
6. A monoclonal antibody which is antibody 64M14.
7. A composition comprising monoclonal antibody 64M14.
8. A method of inhibiting growth of tumor cells, the method comprising contacting the tumor cells with a monoclonal antibody that competes for specific binding to human Jagged 1 with the antibody 64M14 in an amount effective to inhibit tumor cell growth.
9. The method of claim 8 wherein the antibody is conjugated to a cytotoxic moiety.
10. The method of claim 8 further comprising contacting the tumor cells with at least one additional therapeutic agent.
11. The method of claim 10, wherein the additional therapeutic agent is an anti-VEGF antibody.

12. The method of claim 10 wherein the additional therapeutic agent is bevacizumab.

13. The method of claim 8 wherein the tumor cells are from a breast tumor, a colorectal tumor, a lung tumor, a pancreatic tumor, a prostate tumor, or a head and neck tumor.

14. A method of inhibiting growth of tumor cells, the method comprising contacting the tumor cells with monoclonal antibody 64M14.

* * * * *